US009140612B2

(12) United States Patent
Snyder

(10) Patent No.: US 9,140,612 B2
(45) Date of Patent: Sep. 22, 2015

(54) MEASURING SEEBECK COEFFICIENT

(75) Inventor: G. Jeffrey Snyder, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 601 days.

(21) Appl. No.: 13/403,835

(22) Filed: Feb. 23, 2012

(65) Prior Publication Data

US 2012/0213250 A1    Aug. 23, 2012

Related U.S. Application Data

(60) Provisional application No. 61/445,937, filed on Feb. 23, 2011, provisional application No. 61/501,608, filed on Jun. 27, 2011.

(51) Int. Cl.
*G01K 7/00* (2006.01)
*G01K 7/02* (2006.01)
*G01N 25/32* (2006.01)

(52) U.S. Cl.
CPC . *G01K 7/02* (2013.01); *G01N 25/32* (2013.01)

(58) Field of Classification Search
CPC ..................................................... G01K 7/02
USPC ........................................... 374/179, E7.004
See application file for complete search history.

(56) References Cited

U.S. PATENT DOCUMENTS 4,865,462 A * 9/1989 Broomfield .................. 374/179
6,459,069 B1 * 10/2002 Rabinovich .............. 219/121.63
6,467,951 B1 * 10/2002 Ghoshal .......................... 374/45
6,487,515 B1 * 11/2002 Ghoshal ........................ 702/136
7,175,343 B2 * 2/2007 Phillips ......................... 374/180
2005/0023269 A1 * 2/2005 Hiramatsu et al. ......... 219/444.1

FOREIGN PATENT DOCUMENTS

JP        2009258032 A  * 11/2009

OTHER PUBLICATIONS

C. Wood, D. Zoltan, and G. Stapfer, "Measurement of Seebeck coefficient using a light pulse", Review Scientific Instruments, pp. 719-722, vol. 56, No. 5, May 1985.*
C. Wood, A. Chmielewski, and D, Zoftan, "Measurement of Seebeck coefficient using a large thermal gradient", Review Scientific Instruments, pp. 951-954, vol. 59, No. 5, May 1988.*
Wood et al., "Measurement of Seebeck coefficient using a light pulse," Rev. Sci. Instrum. 56 (5), May 1985, pp. 719-722.

(Continued)

*Primary Examiner* — Lisa Caputo
*Assistant Examiner* — Nasir U Ahmed
(74) *Attorney, Agent, or Firm* — Canady & Lortz LLP; Bradley K. Lortz

(57) ABSTRACT

A high temperature Seebeck coefficient measurement apparatus and method with various features to minimize typical sources of errors is described. Common sources of temperature and voltage measurement errors which may impact accurate measurement are identified and reduced. Applying the identified principles, a high temperature Seebeck measurement apparatus and method employing a uniaxial, four-point geometry is described to operate from room temperature up to 1300K. These techniques for non-destructive Seebeck coefficient measurements are simple to operate, and are suitable for bulk samples with a broad range of physical types and shapes.

21 Claims, 10 Drawing Sheets

(56) References Cited

OTHER PUBLICATIONS

Martin et al., "High Temperature Seebeck coefficient metrology," Journal of Applied Physics 108, 121101, Dec. 2010.

Wood et al., "Measurement of Seebeck coefficient using large thermal gradient," Rev. Sci. Instrum. 59 (6), Jun. 1988, pp. 951-954.

* cited by examiner

MEASURING SEEBECK COEFFICIENT

CROSS-REFERENCE TO RELATED APPLICATIONS

This application claims the benefit under 35 U.S.C. §119 (e) of the following U.S. provisional patent applications, which are incorporated by reference herein:

U.S. Provisional Patent Application No. 61/445,937, filed Feb. 23, 2011, and entitled "Apparatus for Measurement of Seebeck Coefficient", by Snyder; and U.S. Provisional Patent Application No. 61/501,608, filed Jun. 27, 2011, and entitled "Apparatus for Measurement of Seebeck Coefficient", by Snyder.

STATEMENT OF GOVERNMENT RIGHTS

The invention described herein was made in the performance of work under a NASA contract, and is subject to the provisions of Public Law 96-517 (35 U.S.C. 202) in which the Contractor has elected to retain title.

BACKGROUND OF THE INVENTION

1. Field of the Invention

This invention relates to determining the Seebeck coefficient for thermoelectric materials. Particularly, this invention relates to measuring the Seebeck coefficient for high temperature thermoelectric materials.

2. Description of the Related Art

An applied temperature difference across a material causes charged carriers in the material (electrons or holes) to diffuse from the hot side to the cold side. Mobile charged carriers migrating from the hot to the cold side leave behind their oppositely charged and immobile nuclei, resulting in a thermoelectric voltage across the material.

The term, "thermoelectric," refers to the fact that the voltage is created by a temperature difference. Since a separation of charges also yields an electric field, the buildup of charged carriers on the cold side eventually ceases at some maximum value for a given temperature difference as there exists an equal amount of charged carriers drifting back to the hot side as a result of the electric field equilibrium. An increase in the temperature difference can result in more charge carriers on the cold side and thus yield an increase in the thermoelectric voltage.

The Seebeck coefficient (or thermopower) is a measure of the magnitude of an induced thermoelectric voltage in response to a temperature difference across a given material. The Seebeck coefficient has units of volts per degrees kelvin.

$$S = \frac{\Delta V}{\Delta T} \quad (1)$$

The Seebeck coefficient, S, depends on a material's temperature, and crystal structure. Typically, metals have small thermopowers because most have half-filled bands, including both electrons and holes. Electrons (negative charges) and holes (positive charges) both contribute to the induced thermoelectric voltage thus tending cancel their contributions to that voltage, resulting in a low net voltage. In contrast, semiconductors can be doped with an excess amount of electrons or holes and therefore can have large positive or negative values of the thermopower depending on the charge of the excess carriers. The sign of the thermopower indicates which charged carriers dominate the electric transport in both metals and semiconductors.

Accurate measurement of the Seebeck coefficient is critical for the performance assessment of thermoelectric materials. High temperature (e.g. greater than 500 C) Seebeck coefficient measurement systems are necessary for efficient and progressive development of thermoelectric materials for waste heat harvesting applications. The history and challenges of Seebeck coefficient measurement has been recently reviewed. See e.g. J. Martin, T. Tritt, and C. Uher, J. Appl. Phys. 108, 121101 (2010), which is incorporated by reference herein.

In view of the foregoing, there is a need in the art for improved apparatuses and methods for accurately measuring the Seebeck coefficient of thermoelectric materials. There is particularly a need for such apparatuses and methods to operate at high temperatures (e.g. above 500 C). Further, there is a need for such apparatuses and methods to be simple, non-destructive, efficient, fast and affordable. There is also a need for such systems and methods to be suitable for bulk material samples in a broad range of physical types and shapes. These and other needs are met by embodiments of the present invention as detailed hereafter.

SUMMARY OF THE INVENTION

A high temperature Seebeck coefficient measurement apparatus and method with various features to minimize typical sources of errors is described. Common sources of temperature and voltage measurement errors which may impact accurate measurement are identified and reduced. Applying the identified principles, a high temperature Seebeck measurement apparatus and method employing a uniaxial, four-point geometry is described to which can operate from room temperature up to approximately 850K or even as high as 1300K in some applications. These techniques for non-destructive Seebeck coefficient measurements are simple to operate, and are suitable for bulk samples with a broad range of physical types and shapes.

A typical embodiment of the invention comprises an apparatus for measuring a Seebeck coefficient of a sample, including a first heater assembly having a first bore therethrough exiting at a first substantially perpendicular surface for contacting and producing a first isothermal sample surface, a first thermocouple having a first axis where temperature and voltage are sensed at an end of the first axis, the first thermocouple disposed in the first bore of the first heater assembly to contact the first isothermal sample surface, a second heater assembly having a second bore therethrough exiting at a second substantially perpendicular surface for contacting and producing a second isothermal sample surface on a sample side opposite the first isothermal sample surface, and a second thermocouple having a second axis where temperature and voltage are sensed at an end of the second axis, the second thermocouple disposed in the second bore of the second heater assembly to contact the second isothermal sample surface. In some embodiments, the first bore and the second bore are aligned such that the first axis of the first thermocouple and the second axis of the second thermocouple are substantially collinear. Compressive springs may be used to apply force to the sample between the first heater assembly and the second heater assembly In some embodiments, the first thermocouple and the second thermocouple may each comprise an electrically insulating cylinder having four bores exiting at an end surface of the cylinder and two thin wires. Each wire is threaded through two of the four bores and crossed to contact each other at the end surface. Typically, the two thin wires may comprise material combinations X/Y of niobium/chromel, niobium/tungsten, niobium/tungsten-rhenium, copper/constantan, or gold-iron/chromel, where X is a first wire material disposed on top of a second wire material Y. In addition, the electrically insulating cylinder of each thermocouple may comprise a ceramic, such as mullite.

In further embodiments, the first heater assembly and the second heater assembly may each comprise an insulating ceramic. In addition, the first heater assembly and the second heater assembly may each comprise a plurality of embedded cartridge heaters.

A typical method embodiment of measuring a Seebeck coefficient of a sample the invention comprises disposing a first heater assembly having a first bore therethrough exiting at a first substantially perpendicular surface to contact the sample and produce a first isothermal sample surface, disposing a second heater assembly having a second bore therethrough exiting at a second substantially perpendicular surface to contact the sample and produce a second isothermal sample surface on a sample side opposite the first isothermal sample surface, measuring temperature of the first isothermal sample surface with a first thermocouple having a first axis where temperature and voltage are sensed at an end of the first axis, the first thermocouple disposed in the first bore of the first heater assembly to contact the first isothermal sample surface, measuring voltage of the first isothermal sample surface with the first thermocouple, measuring temperature of the second isothermal sample surface with a second thermocouple having a second axis where temperature and voltage are sensed at an end of the second axis, the second thermocouple disposed in the second bore of the second heater assembly to contact the second isothermal sample surface, measuring voltage of the second isothermal sample surface with the second thermocouple, and calculating the Seebeck coefficient of the sample from the temperatures and voltages of the first isothermal sample surface and second isothermal sample surface. This method embodiment of the invention may be further modified consistent with the apparatus embodiments described herein.

Another typical embodiment of the invention may comprise a first heater assembly means for contacting and producing a first isothermal sample surface, the first heater means having a first bore therethrough exiting at a first substantially perpendicular surface, a first thermocouple means for measuring temperature and voltage, the first thermocouple means having a first axis where temperature and voltage are sensed at an end of the first axis, the first thermocouple means disposed in the first bore of the first heater assembly means to contact the first isothermal sample surface, a second heater assembly means for contacting and producing a second isothermal sample surface on a sample side opposite the first isothermal sample surface, the second heater assembly means having a second bore therethrough exiting at a second substantially perpendicular surface, and a second thermocouple means for measuring temperature and voltage, the second thermocouple means having a second axis where temperature and voltage are sensed at an end of the second axis and the second thermocouple means disposed in the second bore of the second heater assembly means to contact the second isothermal sample surface. This embodiment of the invention may be further modified consistent with the apparatus or method embodiments described herein.

BRIEF DESCRIPTION OF THE DRAWINGS

Referring now to the drawings in which like reference numbers represent corresponding parts throughout.

DETAILED DESCRIPTION OF THE PREFERRED EMBODIMENT

1. Overview

Figure 1:
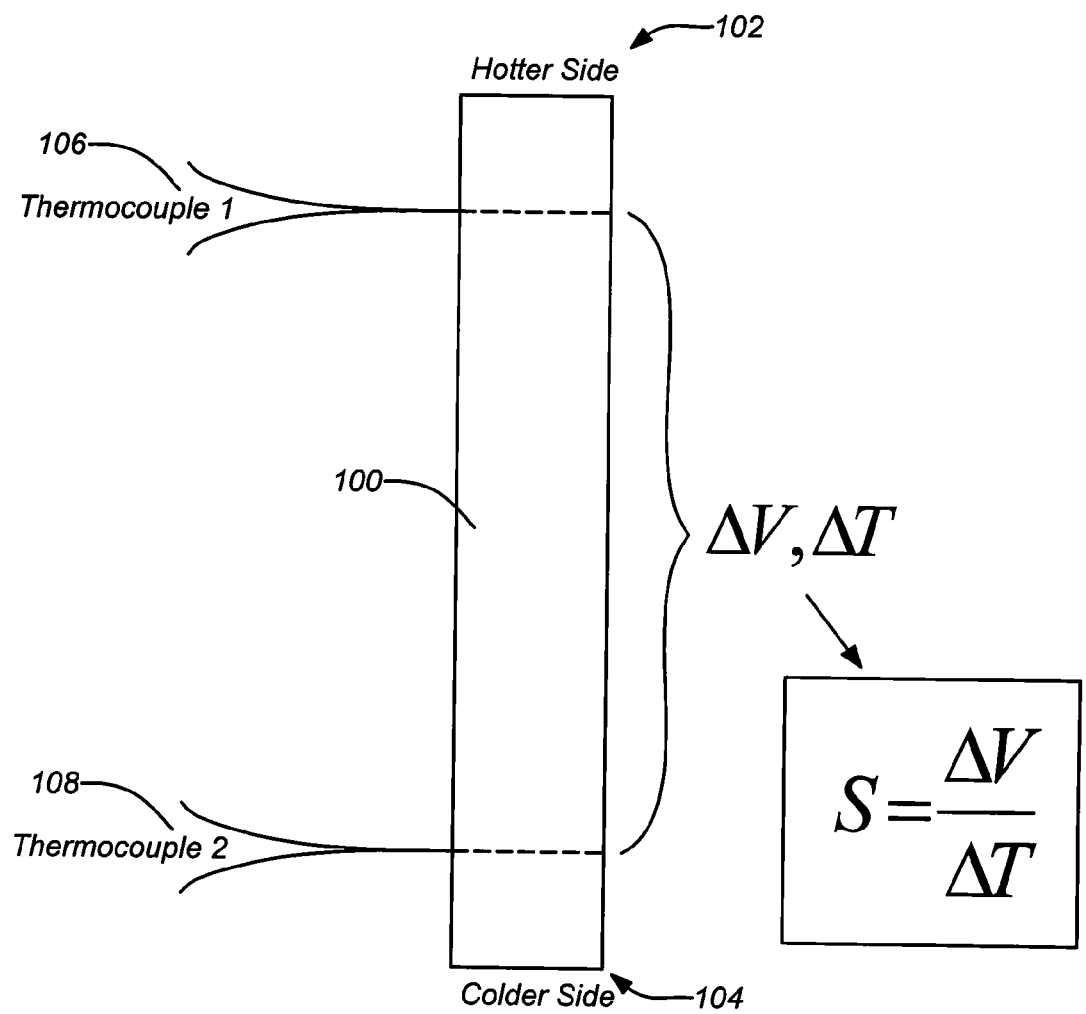
FIG. 1 is a schematic diagram of ideal measurement geometry for the Seebeck coefficient, with thermocouples making small point contacts.

FIG. 1 shows the ideal measurement geometry for the Seebeck coefficient where two probes 106, 108 make point contacts with the sample material 100 at precise locations across a temperature gradient between a hot side 102 and a cold side 104 of the sample material 100. In principle, measurement of the Seebeck coefficient in bulk materials is relatively simple. One needs to know the temperature gradient between two locations on a sample, and the voltage across the two points. The probes 106, 108 serve as both the thermocouples as well as the voltage measurement leads, across which the temperature gradient and voltage present are measured. (It should be noted that for every example measurement system described herein, thermocouples also serve as the voltage measurement leads unless otherwise stated.) For an ideal measurement of the Seebeck coefficient, certain assumptions are applied. First, the system is assumed to be in steady state during the measurement of the temperature and voltage, and that both measurements occur simultaneously. In addition, it is also assumed that the voltage response to the temperature gradient is linear and that the measurement of the temperature and voltage occur at the same point on the sample for each probe.

It should be noted that throughout this description a temperature gradient across a material may be established by two elements, one having a hotter temperature than the other. These elements may be described as either a heater or a cooler depending upon their temperatures relative to the ambient tempurature. However, the term, "heater," will be used generically thoughout this description to mean both the hotter and the colder element used in a system. Measurement of the Seebeck coefficient only concerns their temperatures relative to each other; their temperatures relative to the ambient temperature is not a factor.

However, in a real instrument, non-negligible errors often result due to the inability to achieve these ideal conditions. For example, temperature and voltage measurements often occur at different times in practice. In addition, the voltage response to the temperature gradient is often not linear in practice due to insufficient signal or non-zero voltage at $\Delta T=0$. Furthermore, during high temperature measurements, there is often a noticeable voltage offset that results in significant inaccuracies arising from simple $\Delta V/\Delta T$ measurement. The origin of this voltage offset may be unclear, but it has been found to increase with temperature and can become particularly significant at temperatures greater than 300 C. Finally, true co-location of the measurement of the temperature and voltage is almost never attained, as there is always some distance between the temperature and voltage measurement locations due to the finite size of the temperature sensor. The smallest point source temperature sensor used in Seebeck measurement is a thermocouple. However, in a thermocouple junction, the temperature where the wires meet is not necessarily the same as the sample temperature associated with the voltage measurement.

Having identified the foregoing sources of Seebeck coefficient measurement error, embodiments of the present invention are directed to minimizing these effects in order to obtain more accurate measurements of the Seebeck coefficient.

2. Seebeck Coefficient Measurement Geometries

Since any real instrument setup will deviate from ideal measurement conditions, it is important to consider which geometric design and measurement techniques provide minimum errors. Currently, there are two dominant measurement geometries known in the art, a two-point geometry where thermocouples are embedded in heater and heat sink blocks and an off-axis four-point geometry where thermocouples contact the side of the sample. Two-point geometry refers to the co-location of the thermocouples and the heating and heat sink blocks; heating/cooling and measurement occurs between two points. Four-point geometry refers to a separation between the thermocouples and the heating and heat sink blocks; heating and heat sinks are between two points and measurement occurs between two different points. Off-axis/uniaxial refers to the axes of the thermocouples used to measure the Seebeck coefficient, i.e. whether they are along different axes (off axis) or along a common axis (uniaxial). This terminology is applicable to thermocouples configured with at least a portion having a slender geometry with an identifiable axis where measurement is sensed at one end of the axis. When force is applied to a thermocouple (e.g. by a spring), the direction of the force can define the direction of the axis and the position of the thermocouple defines the position of the axis.

Figure 2A:
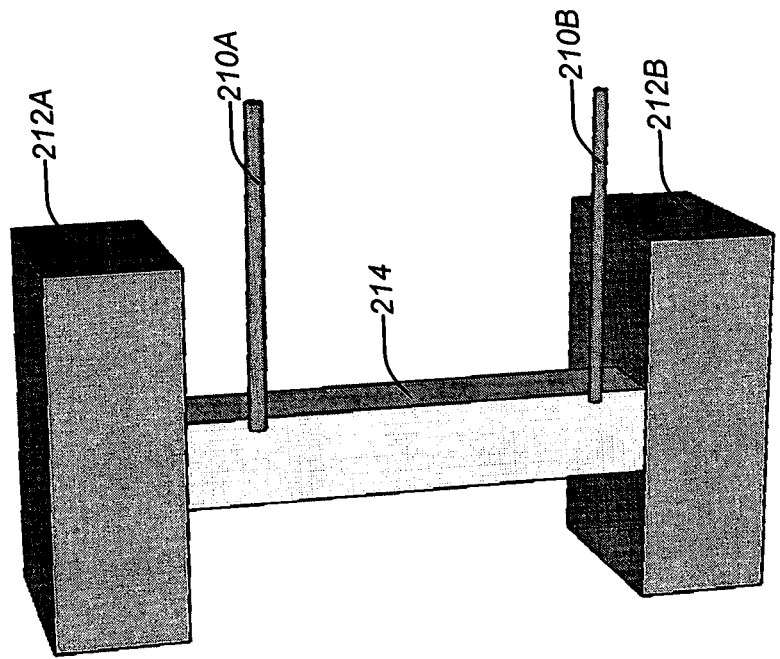
FIG. 2A is a cross-section view of an example two-point geometry where thermocouples are embedded in heater and heat sink blocks for measurement of the Seebeck coefficient.

FIG. 2A is a cross-section view of an example two-point geometry where thermocouples 200A, 200B are embedded in heater and heat sink blocks 202A, 202B for measurement of the Seebeck coefficient. In this geometry, a bulk sample 204 is placed between two metal blocks 202A, 202B, which act as a heat source and a sink, respectively, to establish the thermal gradient. In this case, the thermocouples 200A, 200B are embedded in these blocks 202A, 202B. In this example two-point geometry shown in FIG. 2A, the thermocouple and voltage sensors are embedded into the blocks rather than directly contacting the sample. This setup gives the advantage of avoiding possible chemical reactions between the sample and the thermocouple materials (which will be discussed later) and can accommodate a wide range of sample geometries. However, this system inherently has thermal and electrical contact resistance in these metal blocks themselves, as well as across the interfaces between the sample and the metal blocks. In particular, the thermal contact resistances are often large enough to lead to inaccuracies in the temperature measurement.

Figure 2B:
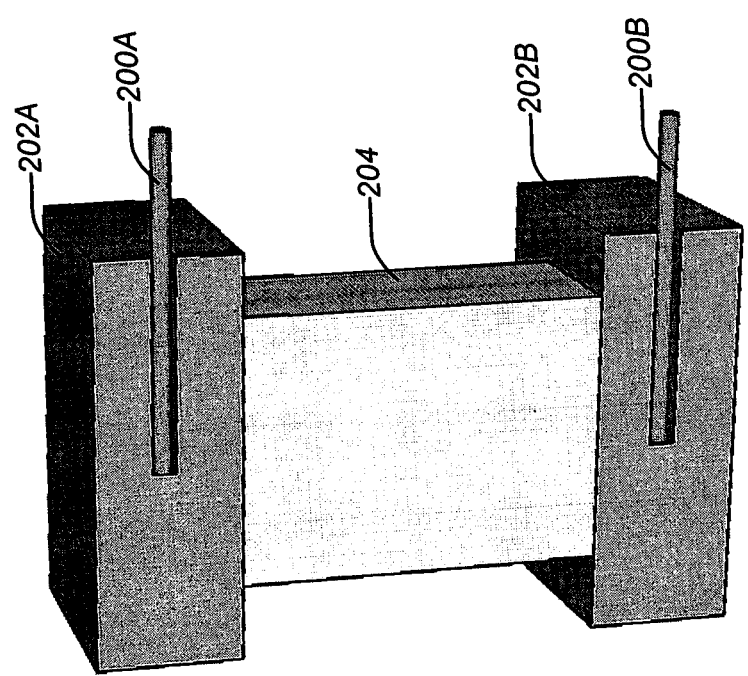
FIG. 2B is a cross-section view of an example off-axis four-point geometry where thermocouples contact the side of the sample for measurement of the Seebeck coefficient.

FIG. 2B is a cross-section view of an example off-axis four-point geometry where thermocouples 210A, 210B contact the side of the sample 214 (i.e. "off" the central axis of the sample) for measurement of the Seebeck coefficient. In this case, a long bar sample 214 is sandwiched between a heater 212A and a heat sink 212B. In this configuration the two thermocouples 210A, 210B contact the sample 214 at two locations along the temperature gradient. This geometry is used by the ZEM line of instruments (Ulvac-Riko Inc., Japan). See http://www.ulvac-riko.co.jp/English/B-9en.html, which is incorporated by reference herein.

It is known that four-point electrical resistance measurements are an improvement on the two-point technique for materials with low electrical impedance. In a similar manner, a four-point thermal design can reduce the effect of thermal contact resistance. Such a design is shown in FIG. 2B, where the key difference from the two-point geometry of FIG. 2A is the placement of the thermocouples along the side of the sample. While this important modification eliminates the thermal contact resistance between the sample and the heat source/sink, several critical issues remain.

Off-axis four-point geometry measurement (e.g. as in the example of FIG. 2B) still presents potential issues which undercut accuracy of the Seebeck coefficient measurement. The first issue typically arises at higher temperatures, where the thermal conductance of the thermocouples can draw heat away from the sample (the so-called "cold-finger effect") leading to a temperature difference across the thermocouple bead. This effect can result in a voltage and temperature measurement dislocation, where with the separate measurements are made at different locations having different temperatures. (This effect is described in further detail hereafter regarding FIG. 3A.) Second, lateral spring loading of the thermocouples into the sample is required to ensure good thermal contact between the thermocouples and the sample surface. At high temperatures, plastic deformation often occurs in softer samples and this can lead to poor thermal contact. On the other hand, side loading can lead to sample fracture or breakage with brittle samples. Furthermore, if low spring forces are used in an attempt to accommodate the side loading issues, high contact resistance between the thermocouple and the sample can result.

An additional issue of off-axis four-point geometry measurement is that it requires that samples be in an elongated geometry to develop a low dT/dz across the thermocouple-sample junctions. (The elongated sample geometry is illustrated between the samples of FIGS. 2A and 2B where the sample 214 has a much small width compared to its length than the other sample 204.) This is necessary since there is uncertainty in the temperature reading if the junction contacts a sample surface that has a temperature gradient. Shaping the sample into an elongated geometry can be difficult for some materials, since the better thermoelectric materials are often brittle. Thus, samples can be damaged during cutting. Furthermore, this geometry is unsuitable for flash diffusivity measurements. This incompatibility often leads to the use of more than one sample to acquire the properties of interest for full characterization, raising the issue of sample-to- sample homogeneity.

3. Improved Seebeck Coefficient Measurement Geometry

Figure 2C:
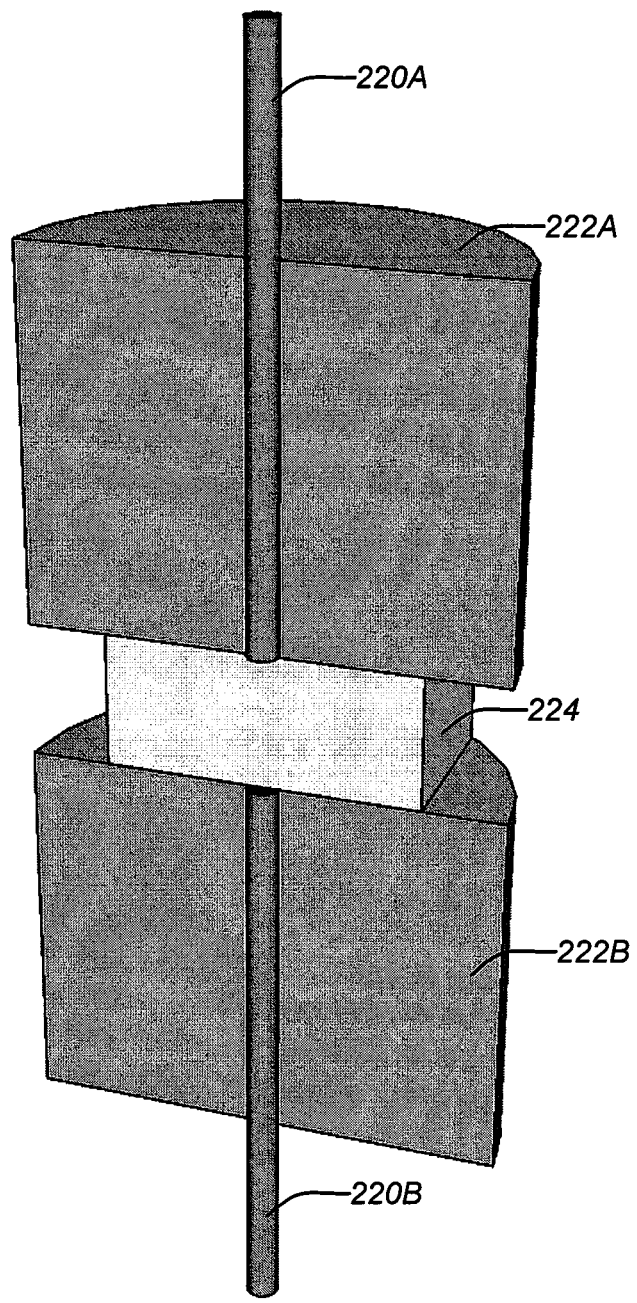
FIG. 2C is a cross-section view of an example uniaxial four-point geometry where thermocouples contact ends of the sample through heater and heat sink blocks for measurement of the Seebeck coefficient.

FIG. 2C is a cross-section view of an example uniaxial four-point geometry where thermocouples 220A, 220B contact ends of the sample 224 through heater 222A and heat sink 222B blocks for measurement of the Seebeck coefficient. This instrument geometry significantly improves some of common problems previously described. The uniaxial four-point Seebeck system concept originates from NASA-JPL in the 1980s when they were developing an apparatus using a light pipe to supply a dynamic ΔT. See C. Wood, D. Zoltan, and G. Stapfer, Rev. Sci. Instrum. 56, 5 (1985), which is incorporated by reference herein. However, Wood et al., does not employ heater assemblies having thermocouples disposed in bores therethrough as described in the present invention. There are three main advantages of employing this geometry. First, thermocouples make direct contacts to the sample surface, while avoiding the "cold-finger effect." Second, thermocouple junctions contact the isothermal temperature surface, providing a very accurate temperature measurement. Third, the uniaxial design allows thermocouples to exert larger forces onto the surface, contributing to the minimization of the thermal and electrical contact resistance.

As shown in FIG. 2C, the cylindrical heater element 222A, which may be constructed from a piece of machinable boron nitride, has a bore through the center. A thermocouple 220A shielded with a four-bore ceramic cylinder, which has a slightly smaller diameter compared to the diameter of the bore, is disposed through the heater element 222A. In this example design, the thermocouple probe tip is heat-sunk to the heaters, thereby reducing cold-finger effects. This configuration is in contrast to the off-axis design of FIG. 2B, where the cold finger effect is exacerbated by the thermocouple-sample contact resistance and the temperature difference between the sample and ambient temperature.

Regarding thermocouple junction contacts, FIG. 2C shows how thermocouple junctions contact the uniform temperature regions of opposite sample surfaces created by a heater and heat sink blocks making an intimate contact with the sample. In each geometry shown in FIGS. 2A-2C, the heaters/heat sinks establish a temperature gradient along the principle axis of the samples. The off-axis geometry of FIG. 2B only allows the finite size thermocouple bead to contact the surface with a temperature gradient. Only the geometry in FIG. 2C allows the thermocouple junction to make contact with an isothermal surface.

An additional benefit with the FIG. 2C geometry of the heaters/heat sinks and thermocouples is that, like the FIG. 2A geometry, a wide range of sample shapes and sizes can be accommodated, with only requirement of having two flat sides substantially parallel to each other. In a typical bulk sample fabrication technique (such as hot press method), a round pellet with a diameter of 10 to 25 mm and thickness of 1 to 2 mm is easily created. This example bulk sample size is convenient because it is in a sample dimension range also required for the hall effect measurement and thermal diffusivity measurement (e.g. using the flash method), other properties typically measured for thermoelectric materials. Further, since the heaters allows exertion of the full ΔT across the sample, even a pellet with thickness as thin as nearly 0.5 mm provides voltage signals measureable with a modern voltage meter.

Finally, the geometry of FIG. 2C also allows all the compressive forces by springs applied along a single principle axis to make good thermo-mechanical contacts with the sample. As will be described in hereafter, the springs attached on the heater assembly may be designed to exert vertical forces onto the sample for good contact between the heaters and the sample surfaces. The compression springs on the back end of thermocouples, which are independent from the heater springs, can apply strong vertical force to the thermocouple junctions against the sample surface. This design is attractive for both brittle and soft materials because the stresses are compressive and no tensile stresses result which might propagate cracks in the sample.

4. Exemplary Thermocouple Design

Here, some features on the thermocouple design incorporated to improve temperature and voltage measurements are addressed. In a typical temperature measurement in high temperature environment, thermocouple types such as S or R, ones that contain platinum wires may be used. In one example setup, however, a thermocouple type which sustains up to approximately 925° K may be used, simply constructed from niobium and chromel wires. There are at least a couple of reasons for this choice.

First, as previously mentioned, a chemical reaction between the thermocouple and the sample may occur at their contact point and adversely affect the Seebeck slope and voltage offset. In order to minimize this effect, thermocouples having minimal reactivity with the sample should be chosen. Platinum thermocouples, while resistant to oxidation, are rather reactive to heavy metals such as Pb, Te, Ag, Bi and Sb. Even nickel has some reactivity with certain thermoelectric elements at high temperatures. Therefore, thermocouple wires that are inert to heavy metals may be preferable.

Another consideration in the selection of a thermocouple type due to the fact that Seebeck coefficient measurement systems typically use one of the thermocouple wires for the voltage measurement. It is noted that the Seebeck effect also occurs in the thermocouple wires, and the voltage reading is a summation of the Seebeck voltages from two wires in addition to the Seebeck voltage from the sample. Although voltages from the wires are opposite in polarity, they do not cancel each other because the magnitudes are not the same: the temperature differences between the contact points and the cold junction of the instruments are different. This residual voltage can falsely increase or decrease the measured Seebeck voltage, depending on the material charge carrier type.

The error induced by this factor is very apparent when measuring low Seebeck coefficient materials with high thermal conductivity (e.g. tungsten). To reduce this effect, a near-zero Seebeck coefficient metal, such as copper or niobium should be used for the voltage probe. This probe is also used as one leg of the thermocouple when combined with a high Seebeck coefficient metal. While the resulting thermocouple supplies only half the voltage of traditional thermocouples, measurement of this reduced signal is well within the capabilities of modern electronics.

For high temperatures, tungsten and niobium have been found to be preferable due to their low reactivity. In one example setup, a combination of niobium and chromium may be used. However, some minor drawbacks may be that these materials must be used in an oxygen free environment and are poor thermocouples for near-room temperature operation. However, embodiments of the invention may be implemented in vacuum or inert atmospheric environments (e.g. Argon, Helium, or Nitrogen). An oxygen environment may be used with proper selection of thermocouple materials (e.g. platinum). Other combinations of thermocouples include niobium/tungsten (up to 1000° C.), niobium/tungsten-rhenium, copper/constantan (type T, up to 350° C.), and gold-iron/chromel.

In order to provide an additional barrier against possible chemical reaction, a thin, flexible, graphite sheet (e.g. Grafoil from GrafTech International Inc, Ohio) may be used between the interface of the sample and thermocouple. With high thermal conductivity (approximately 5 W/mK at room temperature) and low electrical resistivity (approximately 1.15 mΩ·m at room temperature), these sheets also provide good thermal contact between the sample and the heating blocks while not interfering with the voltage measurements.

Figure 3A:
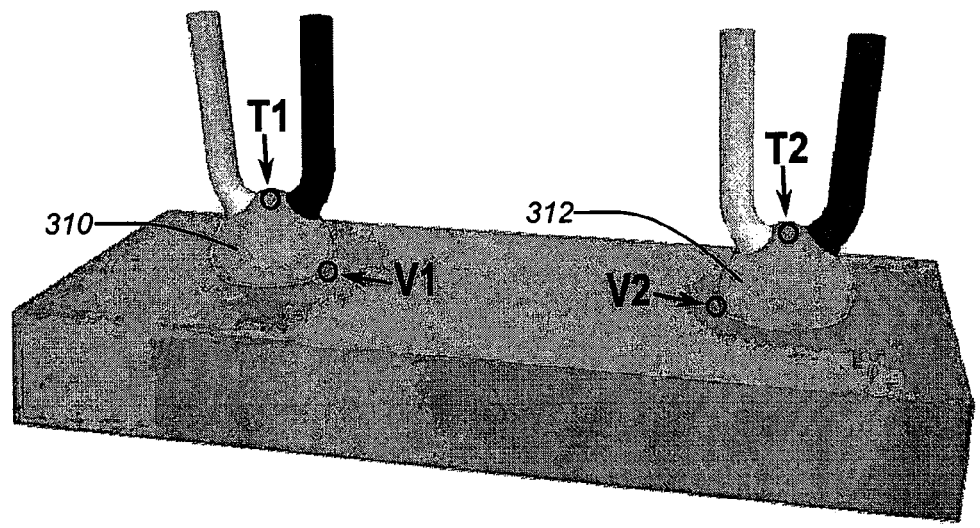
FIG. 3A shows an example of a Seebeck voltage and associated temperature measurement spatial dislocation.

FIG. 3A shows an example of a Seebeck voltage and associated temperature measurement spatial dislocation. This spatial variation can lead to errors when thermal gradients are present across the thermocouple beads 310, 312, the welded joints of the thermocouple. As shown, measured temperatures, T1 and T2, may be located at the tops of the thermocouple beads 310, 312, whereas the measured voltages, V1 and V2, are located at the base of the beads 310, 312 (at different temperatures). While many instruments measuring Seebeck coefficient utilize thermocouples with welded beads as shown in FIG. 3A, novel "crossed-wire" thermocouples described below offer definite advantages.

Figure 3B:
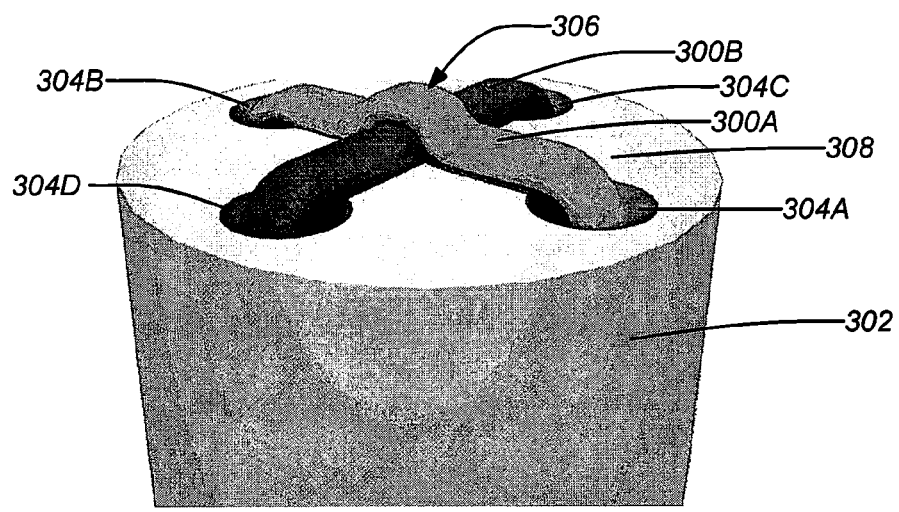
FIG. 3B shows a exemplary crossed-wire geometry may be applied to minimize Seebeck voltage and associated temperature measurement spatial dislocation.

FIG. 3B shows an exemplary crossed-wire geometry may be applied to minimize Seebeck voltage and associated temperature measurement spatial dislocation. In one example crossed geometry, two wires 300A, 300B (e.g. one niobium and one chromel) are made to cross threaded down a four-bore ceramic cylinder 302. Each wire 300A (or 300B) is threaded up one bore 304A (or 304C) and across the end surface 308 and back down an opposing bore 304B (or 304D). Here, the contact between the wires 300A, 300B is mechanical only (not welded) and governed only by the geometry of the crossed wires 300A, 300B. To minimize the temperature gradients across the thermocouple junction region, extremely thin (e.g. 0.1 mm diameter) wires 300A, 300B may be used. In contrast, thermocouple beads (e.g. in FIG. 3A) are typically approximately 1 mm in diameter. To further ensure that the junction is nearly isothermal, the ceramic cylinder 302 used to house the wires may be made of low thermal conductivity mullite (e.g. approximately 1.7 mm diameter). Although such a thin mullite cylinder may be delicate, the force loading is strictly compressive and along the length of the cylinder 302. The example cross-wire geometry may be employed with the configuration of FIG. 2C where the cross-wire contacts are disposed at the end surface of the uniaxial thermocouples 220A, 220B in contact with the sample 224. One wire 300A lies directly over the other wire 300B at their contact point 306. In forming the two-wire thermocouple, the wire 300A material having the lower Seebeck coefficient of the two materials is disposed on top of the wire 300B material having the higher Seebeck coefficient, so that the lower Seebeck coefficient wire makes contact with the sample to minimize measurement error. This top wire 300A is also used to make the voltage measurement. (The top surface of the top wire 300A above the contact point 306 will be the contact point to the sample 224 at the end of each thermocouple 220A, 220B.) The crossed-wire design is additionally advantageous as it avoids the alloying and embrittlement typically associated with welding beads. The ability to simply and rapidly develop new thermocouple wire material combinations is a final advantage delivered by this geometry.

5. Exemplary Seebeck Coefficient Measurement Apparatus

Figure 4A:
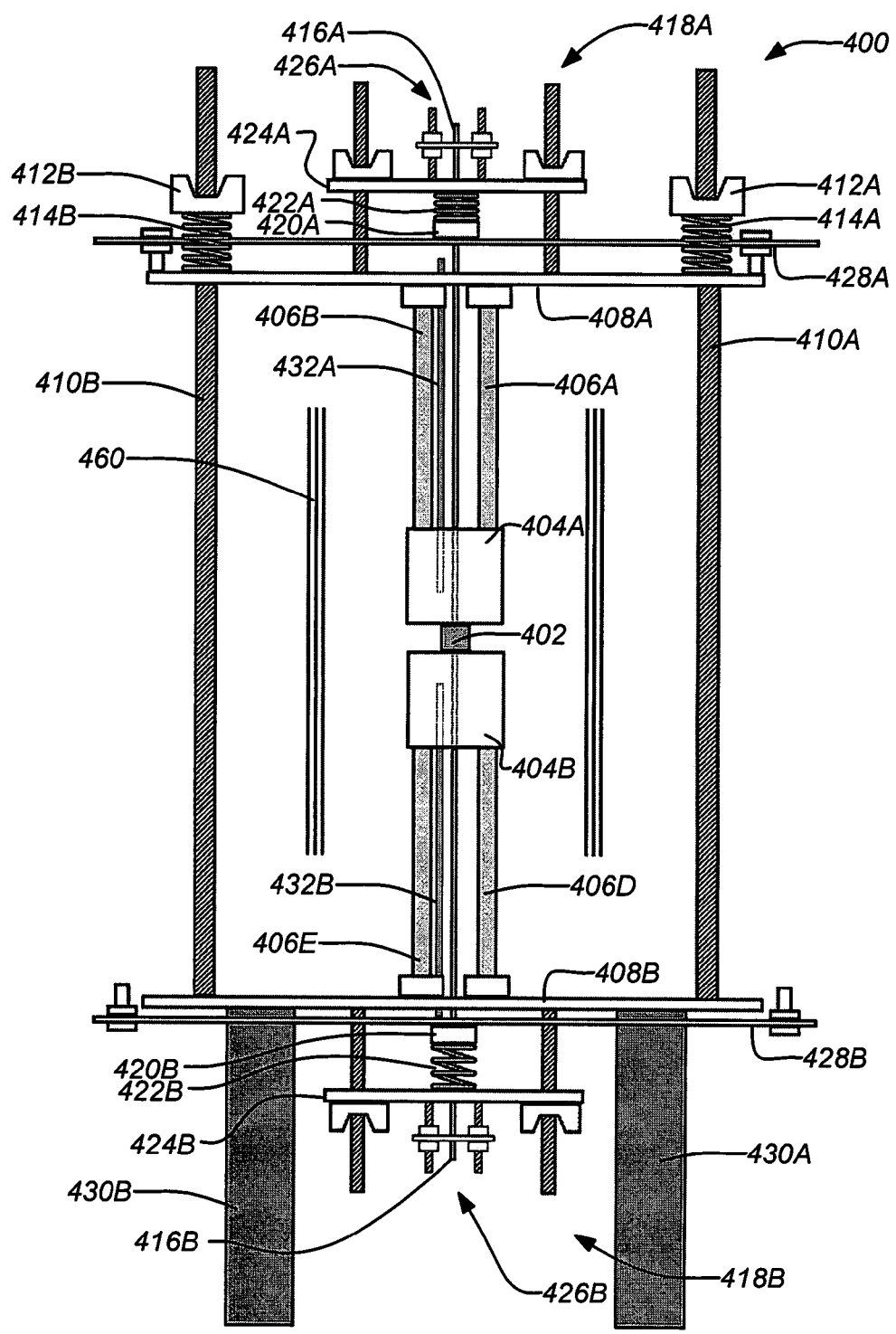
FIG. 4A is a schematic drawing of an exemplary uniaxial four-point Seebeck coefficient measurement instrument.
Figure 4B:
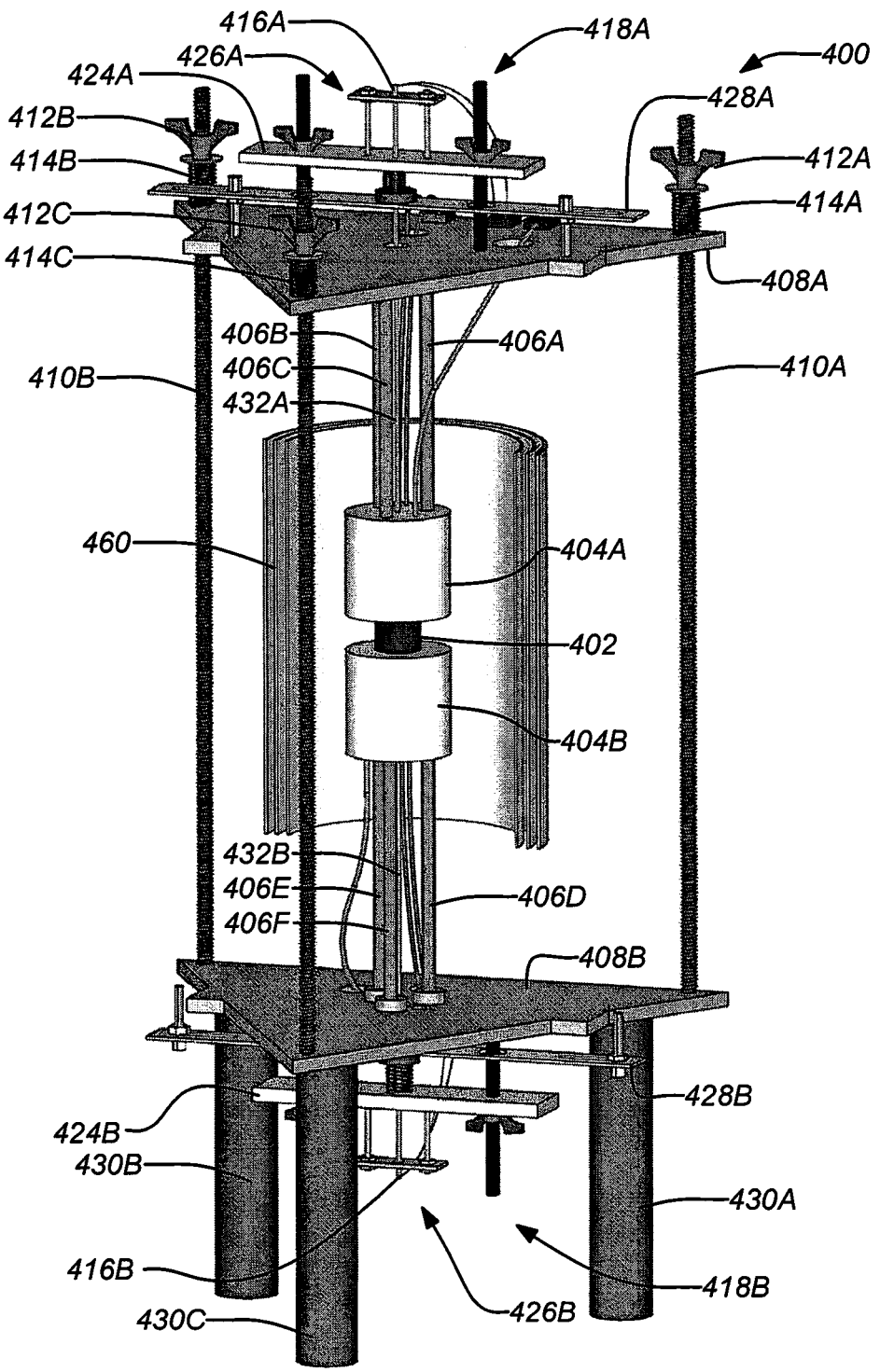
FIG. 4B is a three-dimensional drawing of the exemplary uniaxial four-point Seebeck coefficient measurement instrument.
Figure 4C:
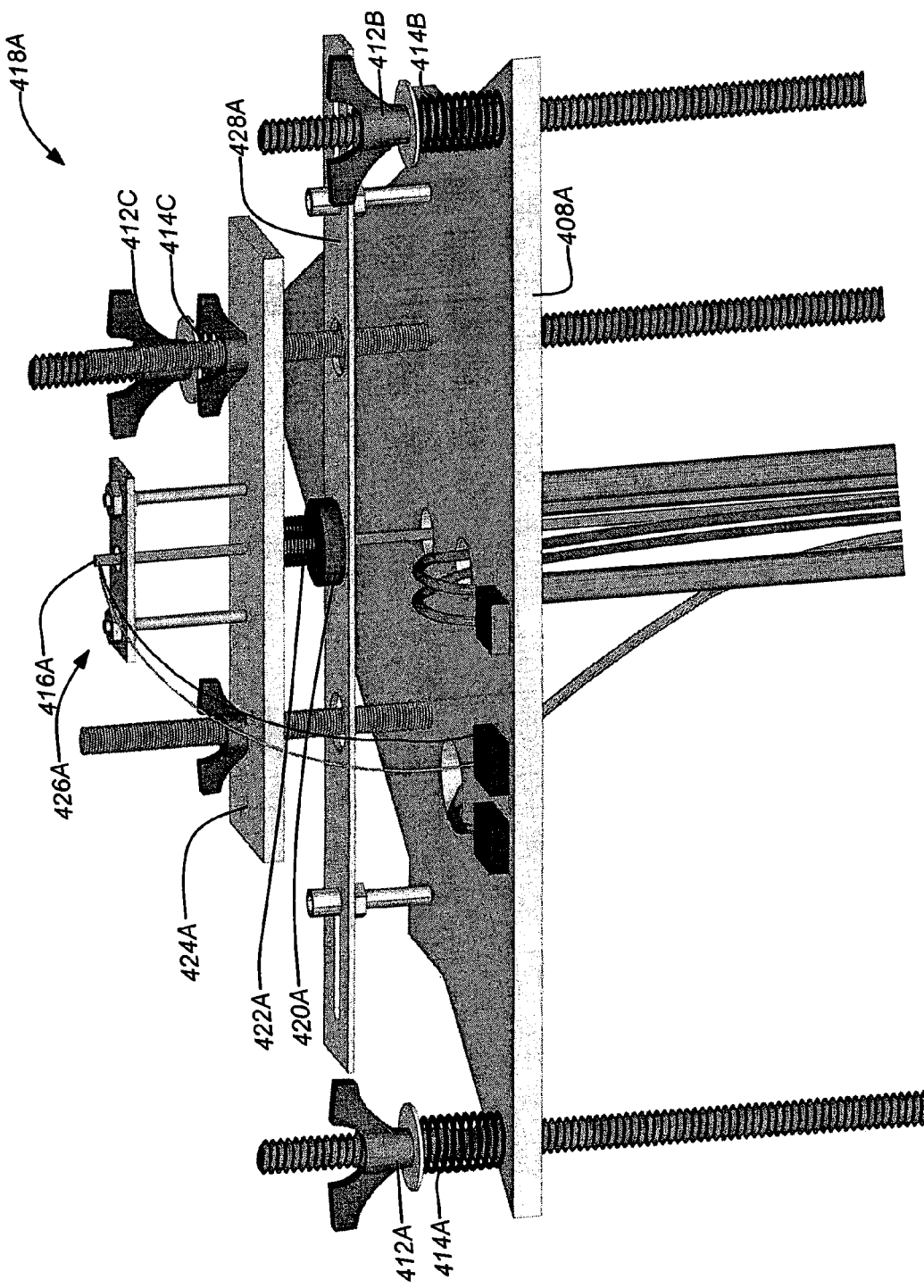
FIG. 4C is a detailed three-dimensional drawing of the thermocouple compression assembly of the upper plate of the exemplary uniaxial four-point Seebeck coefficient measurement instrument.

FIGS. 4A-4C show an exemplary apparatus 400 embodiment for high temperature Seebeck coefficient measurements. FIG. 4A is a schematic drawing of an exemplary uniaxial four-point Seebeck coefficient measurement apparatus 400. FIG. 4B is a three-dimensional drawing of the exemplary uniaxial four-point Seebeck coefficient measurement apparatus 400. FIG. 4C is a detailed three-dimensional drawing of the thermocouple compression assembly of the upper plate of the exemplary uniaxial four- point Seebeck coefficient measurement apparatus 400. Note that for visual simplicity, one leg (of three) of the fixture shown in FIG. 4B is not shown in FIG. 4A.

This uniaxial four-point geometry measurement apparatus 400 employs a horizontal mirror plane through the center of the sample 402. The sample 402 is in contact with two boron nitride cylinder heater assemblies 404A, 404B which each have a ring of a plurality of embedded cartridge heaters (e.g., six), installed parallel to the sidewalls of the cylinders. The cartridge heaters are electrically powered and may be controlled with feedback from separate thermocouples 432A, 432B embedded in each heater assembly 404A, 404B. This annular, symmetric heater cartridge placement around the contact area allows uniform distribution of heat to the sample. Boron nitride of the heater assemblies 404A, 404B satisfies the need for an insulating, chemically inert contact and additionally provides high thermal conductivity. However, the heater assemblies may be formed from any other suitable insulating ceramic material such as alumina, "machineable ceramics," silicon carbide. In addition, some metals may also be used, provided the sample 402 and thermocouples 416A, 416B are electrically insulated from ground (by either electrically insulating these elements from the metal heater block or by electrically insulated the metal heater block from the remainder of the apparatus). Thin walled Inconel (Special Metals Corporation Inc., New York) cylinders 406A-406F are threaded into each heater assembly 404A, 404B and coupled to baseplates 408A, 408B at the upper and lower ends via collar clamps. This adjustable, three-legged geometry ensures good mating between the upper and lower heater assemblies 404A, 404B. The upper and lower baseplates 408A, 408B are aligned through the use of a framework rod 410A-410C at each corner. Compressive force is exerted on the baseplates 408A, 408B, which is carried through to the sample 402, from springs 414A- 414C controlled by wingnuts 412A-412C attached to the framework rods 410A-410C above the upper baseplate 408A. Together, the elements of the assembly immobilize the sample 402 and achieve superior thermal contact with the heater assemblies 404A, 404B.

For the measurement of the Seebeck coefficient, long (e.g. 20 cm) crossed-wire thermocouples 416A, 416B travel along the central axis of the instrument to the sample 402. The thermocouple wires are contained within four-bore mullite cylinder, 1/16 inch in diameter, as previously described in detail in FIG. 3B. Mullite may be chosen because it has lower thermal conductivity compared to alumina, which is the typical material of choice. From the sample 402, each thermocouple 416A, 416B passes through a boron nitride heater assembly 404A, 404B, a baseplate 406A, 406B and into a thermocouple compression assembly (TCA) 418A, 418B at the upper and lower ends of the apparatus 400.

The purpose of the TCA 418A, 418B is to provide low thermal contact resistance between the sample 402 and the thermocouples 416A, 416B. The TCA 418A, 418B allows forces to be independently applied to the thermocouples 416A, 416B (with even greater pressure) than the springs 414A-414C acting against the heater assemblies. Attached to each thermocouple 416A, 416B is a collar clamp 420A, 420B which provides a surface for a spring 422A, 422B to contact and apply force to the thermocouple 416A, 416B. An adjustable plate 424A, 424B in the center of the TCA sets the compression on this spring 422A, 422B. The uppermost assembly 426A, 426B in the TCA provides structural support to the thermocouple 416A, 416B in case of shearing force being inadvertently applied by the operator. When changing samples 402, the spring 422A, 422B within the TCA exerts a force on the collar clamp 420A, 420B and which can drive the thermocouple 416A, 416B tip past the heater assembly 404A, 404B. Such motion exposes the thermocouple 416A, 416B tip, which is mechanically weak and may readily fracture. To avoid this motion, the opposing plate 428A, 428B on the TCA is used to compress the spring 422A, 422B when the sample 402 is replaced. For the purposes of illustration, the upper TCA 418A shows this plate engaged, while the lower TCA 418B shows the plate when the collar clamp is free to move. The measurement assembly 400 may be supported on three legs 430A-430C which are sufficiently long to provide access to the lower TCA 418B.

For PID temperature control, the boron nitride cylinders of the heater assemblies 404A, 404B may have additional thermocouples 432A, 432B embedded in them. These thermocouples 432A, 432B are not used to measure the Seebeck coefficient, but are used instead for temperature control of heater assemblies 404A, 404B.

Figure 4D:
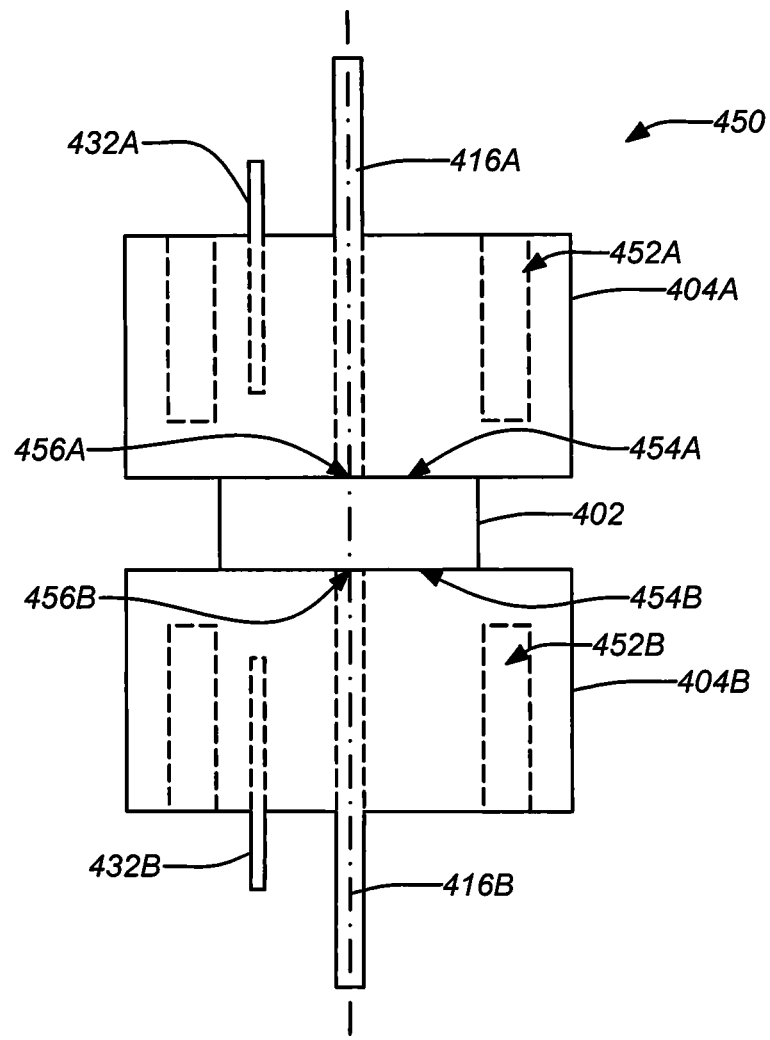
FIG. 4D is a schematic diagram of an exemplary measurement apparatus embodiment of the invention to illustrate some of the fundamental features included in the detailed apparatus of FIGS. 4A-4C.

FIG. 4D is a schematic diagram of an exemplary measurement apparatus 450 embodiment of the invention to illustrate some of the fundamental features included in the detailed apparatus 400 of FIGS. 4A-4C. The elements of this apparatus 450 and those of apparatus 400 are interchangeable and functionally consistent. The sample 402 is disposed between two heater assemblies 404A, 404B. Each heater assembly 404A, 404B may comprise a cylinder element, e.g. of boron nitride. A plurality of cartridge heaters 452A, 452B are embedded in each of the heater assemblies 404A, 404B. Although any suitable number of cartridge heaters or other suitable heating device may be used, in one example six cartridge heaters may be embedded in each heater assembly 404A, 404B in a radial pattern. Pressure between the heater assemblies 404A, 404B and the sample 402 is applied and controlled by compression springs 414A-414C of the supporting structure (as described regarding FIGS. 4A-4C). The heater assemblies 404A, 404B are operated to establish isotherm at opposite surfaces 454A, 454B of the sample 402. Separate thermocouples 432A, 432B may be embedded in each of the heater assemblies 404A, 404B in order to monitor their temperatures.

Long cylindrical thermocouples 416A, 416B are disposed within bores through each of the heater assemblies 404A, 404B. The heater assemblies 404A, 404B are aligned such that axes of the thermocouples 416A, 416B are substantially collinear. Each thermocouple comprises an electrically insulating cylinder having four bores exiting at an end surface 456A, 456B of the cylinder. Two thin wires are threaded through two of the four bores and cross to contact each other at the end surface 456A, 456B. See FIG. 3B. Pressure between the thermocouples 416A, 416B and the sample 402 is applied and controlled by other compression springs 422A, 422B of the supporting structure (as described regarding FIGS. 4A-4C).

Figure 5:
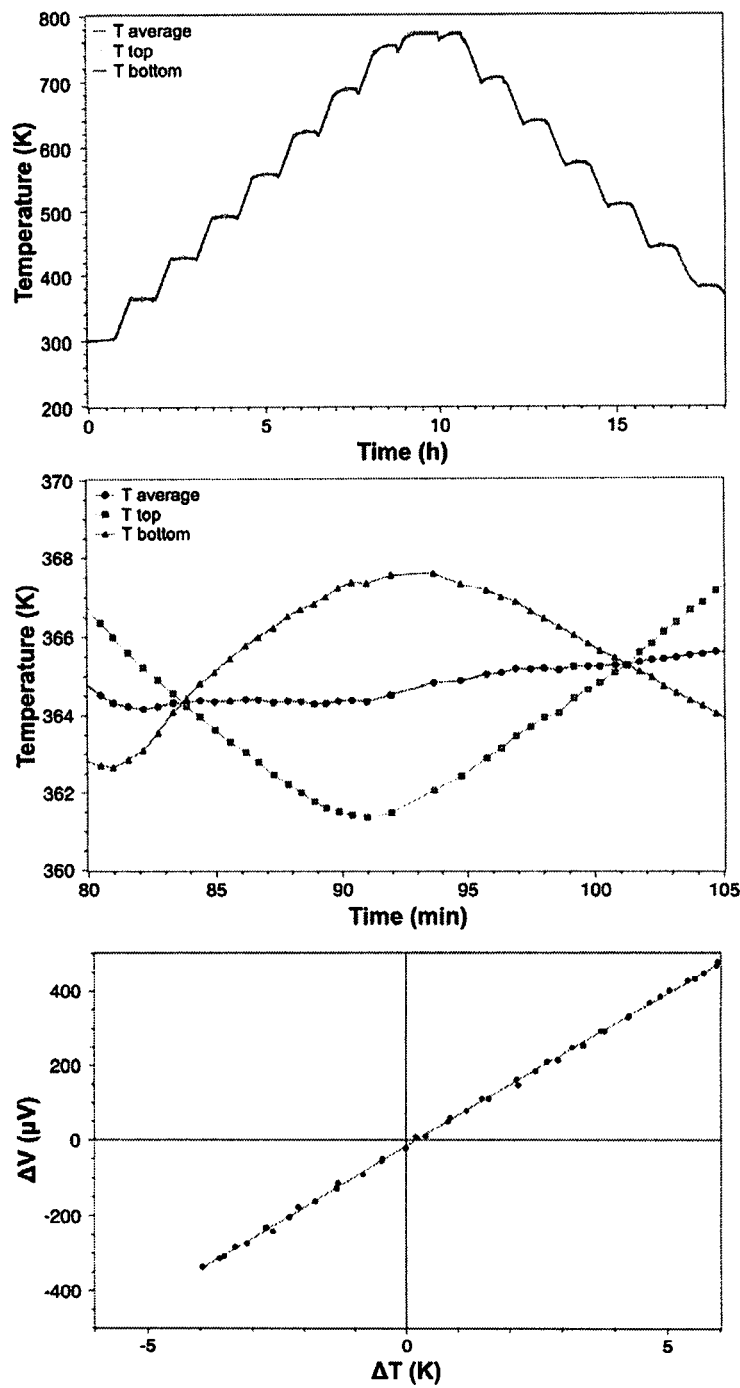
FIG. 5 shows plots of exemplary test results of the top and bottom temperature of the sample applying different temperature gradients, and the resulting derived Seebeck coefficient as the slope of the voltage response.

FIG. 5 shows plots of exemplary test results of the top and bottom temperature of the sample applying different temperature gradients, and the resulting derived Seebeck coefficient as the slope of the voltage response. These plots show temperature oscillations in an example high temperature run. The temperatures shown in the top two plots are taken from the Seebeck measurement thermocouples 416A, 416B. For measurements at each temperature, the temperature gradient is oscillated using the heater assemblies 404A, 404B about a fixed average temperature, as shown in FIG. 5B. The resulting voltage response to the temperature gradient is shown in FIG. 5C, and reveals a substantially linear relationship with the slope as the value of Seebeck coefficient.

Several benefits are worth noting regarding this particular exemplary Seebeck coefficient measurement apparatus 400 design. The apparatus portion above an imaginary horizontal mirror plane through the center of the sample, including the thermocouple compression assembly (TCA), is assembled in one piece, and it can be manually moved vertically when mounting a sample. Its vertical range of movement is guided by framework rods 410A-410C that pass through three holes located at the three corners of the triangular upper baseplate 408A. Since these holes are larger than the diameter of the framework rods 410A-410C, there is allowance for the upper plate assembly (all the elements above the upper baseplate 408A) to be positioned against a sample surface having some anglular deviation from horizontal. Thus, the flexibility of the design allows better contacts between the sample 402 and the heater asemblies 404A, 404B when the sample surfaces are not exactly parallel.

In addition, all springs are located distant from the sample heating area, so that they do not lose compression due to heating. This uniaxial design also affords some clearance around the sample heating area. Accordingly, a cylindrical heat shield 460 or clam-shell furnace may be disposed around the sample heating area. This heat shield 460 can help ensure uniform heating near the sample area.

6. Exemplary Method of Measuring the Seebeck Coefficient

Figure 6:
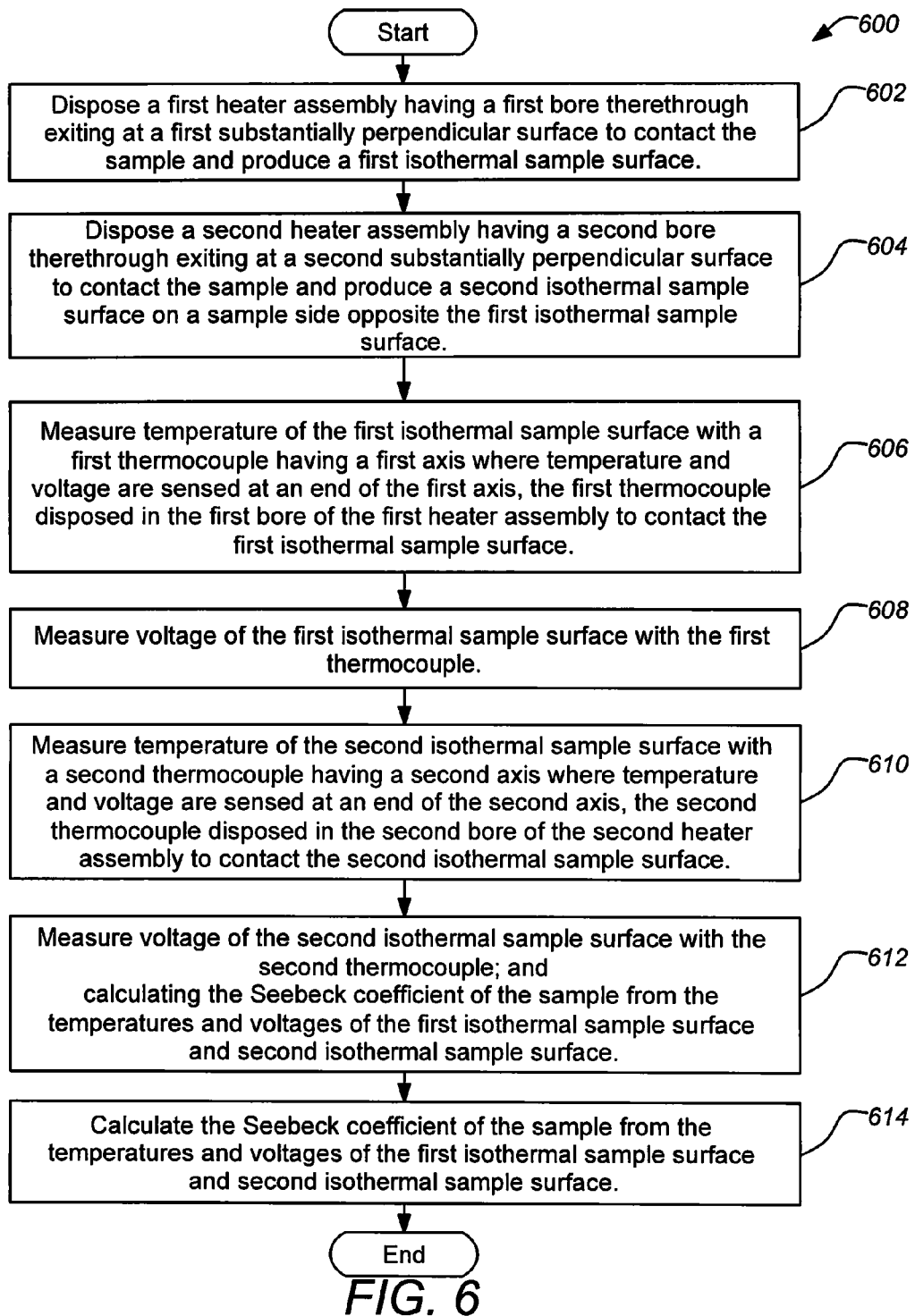
FIG. 6 is a flowchart of an exemplary method of measuring the Seebeck coefficient according to an embodiment of the invention.

FIG. 6 is a flowchart of an exemplary method 600 of measuring the Seebeck coefficient. The method 600 includes an operation 602 of disposing a first heater assembly having a first bore therethrough exiting at a first substantially perpendicular surface to contact the sample and produce a first isothermal sample surface. In operation 604 a second heater assembly having a second bore therethrough exiting at a second substantially perpendicular surface is disposed to contact the sample and produce a second isothermal sample surface on a sample side opposite the first isothermal sample surface. In operation 606 temperature of the first isothermal sample surface is measured with a first thermocouple having a first axis where temperature and voltage are sensed at an end of the first axis, the first thermocouple disposed in the first bore of the first heater assembly to contact the first isothermal sample surface. In operation 608, voltage of the first isothermal sample surface is measured with the first thermocouple. In operation 610, temperature of the second isothermal sample surface is measured with a second thermocouple having a second axis where temperature and voltage are sensed at an end of the second axis, the second thermocouple disposed in the second bore of the second heater assembly to contact the second isothermal sample surface. In operation 612, voltage of the second isothermal sample surface is measured with the second thermocouple. Finally in operation 614, the Seebeck coefficient of the sample is calculated from the temperatures and voltages of the first isothermal sample surface and second isothermal sample surface.

This method 600 may be altered consistent with the various apparatus embodiments previously described. It is important to note that the steps may be performed in any suitable order. In addition, although simultaneous measurement of temperature and voltage is ideal, it is not required and timing of the measurements may be manipulated to improve results as discussed hereafter.

Beyond the example measurement apparatus structures previously described, the measurement process can be altered to further improve accuracy in determining steady-state measurements of the Seebeck coefficient. As previously discussed, ideally all steady state measurements should occur simultaneously. In practice, measurements of temperature and voltage are often conducted sequentially, however. A first-order correction to thermal drift may be achieved by using the delta method, where measurements are symmetric with time. See V.H. Weiss, Z. Naturforsch. B 11a, 131 (1965), which is incorporated by reference herein. For example, measurements taken in the order $T_{c1}$, $T_{h1}$, V, $T_{h2}$, $T_{c2}$ at equally spaced intervals in time to account for linear drift when $T_c = (T_{c1}+T_{c2})/2$ and $T_h=(T_{h1}+T_{h2})/2$. This technique of taking temperature and voltage measurements symmetric with time may be applied directly to the method 600 of measuring the Seebeck coefficient as will be understood by those skilled in the art.

The multiple gradient method measures the voltage difference for various ΔTs (both positive and negative) with the same average temperature of the sample. Non-linear behavior using the multiple gradient technique can be indicative of a poor signal-to-noise ratio, requiring larger ΔT. A ΔT of 3% of the absolute sample temperature is often appropriate, for example.

This concludes the description including the preferred embodiments of the present invention. The foregoing description including the preferred embodiment of the invention has been presented for the purposes of illustration and description. It is not intended to be exhaustive or to limit the invention to the precise forms disclosed. Many modifications and variations are possible within the scope of the foregoing teachings. Additional variations of the present invention may be devised without departing from the inventive concept as set forth in the following claims.

What is claimed is:

1. An apparatus for measuring a Seebeck coefficient of a sample, comprising:
    a first heater assembly having a first bore therethrough exiting at a first substantially perpendicular surface for contacting and producing a first isothermal sample surface;
    a first thermocouple having a first axis of a first slender geometry where temperature and voltage are sensed at an end of the first axis, the first thermocouple disposed in the first bore of the first heater assembly to contact the first isothermal sample surface;
    a second heater assembly having a second bore therethrough exiting at a second substantially perpendicular surface for contacting and producing a second isothermal sample surface on a sample side opposite the first isothermal sample surface; and
    a second thermocouple having a second axis of a second slender geometry where temperature and voltage are sensed at an end of the second axis, the second thermocouple disposed in the second bore of the second heater assembly to contact the second isothermal sample surface.

2. The apparatus of claim 1, wherein the first bore and the second bore are aligned such that the first axis of the first thermocouple and the second axis of the second thermocouple are substantially collinear.

3. The apparatus of claim 1, wherein the first thermocouple and the second thermocouple each comprise an electrically insulating cylinder having four bores exiting at an end surface of the cylinder and two thin wires, each wire threaded through two of the four bores and crossing to contact each other at the end surface.

4. The apparatus of claim 3, wherein the two thin wires comprise material combinations X/Y of niobium/chromel, niobium/tungsten, niobium/tungsten-rhenium, copper/constantan, or gold-iron/chromel, where X is a first wire material disposed on top of a second wire material Y.

5. The apparatus of claim 3, wherein the electrically insulating cylinder comprises a ceramic.

6. The apparatus of claim 5, wherein the ceramic comprises mullite.

7. The apparatus of claim 1, wherein the first heater assembly and the second heater assembly each comprise an insulating ceramic.

8. The apparatus of claim 1, wherein the first heater assembly and the second heater assembly each comprise a plurality of embedded cartridge heaters.

9. The apparatus of claim 1, further comprising compressive springs to apply force to the sample between the first heater assembly and the second heater assembly.

10. A method of measuring a Seebeck coefficient of a sample comprising the steps of:
    disposing a first heater assembly having a first bore therethrough exiting at a first substantially perpendicular surface to contact the sample and produce a first isothermal sample surface;
    disposing a second heater assembly having a second bore therethrough exiting at a second substantially perpendicular surface to contact the sample and produce a second isothermal sample surface on a sample side opposite the first isothermal sample surface;
    measuring temperature of the first isothermal sample surface with a first thermocouple having a first axis of a second slender geometry where temperature and voltage are sensed at an end of the first axis, the first thermocouple disposed in the first bore of the first heater assembly to contact the first isothermal sample surface;
    measuring voltage of the first isothermal sample surface with the first thermocouple; measuring temperature of the second isothermal sample surface with a second thermocouple having a second axis of a second slender geometry where temperature and voltage are sensed at an end of the second axis, the second thermocouple disposed in the second bore of the second heater assembly to contact the second isothermal sample surface;
    measuring voltage of the second isothermal sample surface with the second thermocouple; and calculating the Seebeck coefficient of the sample from the temperatures and voltages of the first isothermal sample surface and second isothermal sample surface.

11. The method of claim 10, wherein the Seebeck coefficient is calculated from temperature and voltage measurements taken symmetric with time.

12. The method of claim 10, further comprising aligning the first bore and the second bore such that the first axis of the first thermocouple and the second axis of the second thermocouple are substantially collinear.

13. The method of claim 10, wherein the first thermocouple and the second thermocouple each comprise an electrically insulating cylinder having four bores exiting at an end surface of the cylinder and two thin wires, each wire threaded through two of the four bores and crossing to contact each other at the end surface.

14. The method of claim 13, wherein the two thin wires comprise material combinations X/Y of niobium/chromel, niobium/tungsten, niobium/tungsten-rhenium, copper/constantan, or gold-iron/chromel, where X is a first wire material disposed on top of a second wire material Y.

15. The method of claim 13, wherein the electrically insulating cylinder comprises an insulating ceramic.

16. The method of claim 15, wherein the ceramic comprises mullite.

17. The method of claim 10, wherein the first heater assembly and the second heater assembly each comprise boron nitride.

18. The method of claim 10, wherein the first heater assembly and the second heater assembly each comprise a plurality of embedded cartridge heaters.

19. The method of claim 10, further comprising compressive springs to apply force to the sample between the first heater assembly and the second heater assembly.

20. An apparatus, comprising:
- a first heater assembly means for contacting and producing a first isothermal sample surface, the first heater means having a first bore therethrough exiting at a first substantially perpendicular surface;
- a first thermocouple means for measuring temperature and voltage, the first thermocouple means having a first axis of a second slender geometry where temperature and voltage are sensed at an end of the first axis, the first thermocouple means disposed in the first bore of the first heater assembly means to contact the first isothermal sample surface;
- a second heater assembly means for contacting and producing a second isothermal sample surface on a sample side opposite the first isothermal sample surface, the second heater assembly means having a second bore therethrough exiting at a second substantially perpendicular surface; and
- a second thermocouple means for measuring temperature and voltage, the second thermocouple means having a second axis of a second slender geometry where temperature and voltage are sensed at an end of the second axis and the second thermocouple means disposed in the second bore of the second heater assembly means to contact the second isothermal sample surface.

21. The apparatus of claim 20, wherein the first thermocouple means and the second thermocouple means each comprise an electrically insulating cylinder having four bores exiting at an end surface of the cylinder and two thin wires, each wire threaded through two of the four bores and crossing to contact each other at the end surface.

* * * * *